(12) United States Patent
Eizenga

(10) Patent No.: US 8,440,875 B1
(45) Date of Patent: May 14, 2013

(54) METHOD AND APPARATUS FOR HIGH ACID CONTENT FEED FOR MAKING DIESEL AND AVIATION FUEL

(75) Inventor: Donald A. Eizenga, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/474,794

(22) Filed: May 18, 2012

(51) Int. Cl.
*C07C 1/20* (2006.01)
*C10G 49/18* (2006.01)

(52) U.S. Cl.
USPC ........... 585/733; 585/734; 585/310; 585/737; 208/263

(58) Field of Classification Search .................. None
See application file for complete search history.

(56) References Cited

U.S. PATENT DOCUMENTS

| | | | |
|---|---|---|---|
| 2,686,794 A | 8/1954 | Clayton | |
| 2,939,790 A | 6/1960 | Clayton | |
| 3,016,336 A * | 1/1962 | Scott et al. | 435/174 |
| 3,095,307 A * | 6/1963 | Scott et al. | 426/8 |
| 2010/0068108 A1 | 3/2010 | Devic | |
| 2011/0094149 A1* | 4/2011 | Weiss et al. | 44/308 |
| 2011/0166405 A1* | 7/2011 | Van Beijnum et al. | 585/733 |
| 2012/0028341 A1 | 2/2012 | Heerze | |

* cited by examiner

*Primary Examiner* — Tam M Nguyen
(74) *Attorney, Agent, or Firm* — David J. Piasecki

(57) ABSTRACT

A method of making a diesel fuel from a renewable feedstock is described. Ammonia or an amine compound is used to neutralize the organic acids in the renewable feedstock. The ammonia or amine compound is removed from the product mixture before the isomerization zone so that it does not affect the isomerization catalyst.

20 Claims, 2 Drawing Sheets

METHOD AND APPARATUS FOR HIGH ACID CONTENT FEED FOR MAKING DIESEL AND AVIATION FUEL

FIELD OF THE INVENTION

This invention relates to a process for producing diesel and aviation boiling range hydrocarbons useful as fuel from renewable feedstocks such as the glycerides and free fatty acids found in materials such as plant oils, animal oils, animal fats, and greases.

BACKGROUND OF THE INVENTION

As the demand for fuels such as aviation fuel increases worldwide, there is increasing interest in sources other than petroleum crude oil for producing the fuel. One source is renewable feedstocks including, but not limited to, plant oils such as corn, jatropha, camelina, rapeseed, canola, soybean and algal oils, animal fats such as tallow, fish oils, and various waste streams such as yellow and brown greases and sewage sludge. The common feature of these feedstocks is that they are composed of mono- di- and tri-glycerides, and free fatty acids (FAA). Another class of compounds appropriate for these processes is fatty acid alkyl esters (FAAE), such as fatty acid methyl ester (FAME) or fatty acid ethyl ester (FAEE). These types of compounds contain aliphatic carbon chains generally having from about 8 to about 24 carbon atoms. The aliphatic carbon chains in the glycerides, FFAs, or FAAEs can be saturated or mono-, di- or poly-unsaturated. Most of the glycerides in the renewable feed stocks will be triglycerides, but some may be monoglycerides or diglycerides. The monoglycerides and diglycerides can be processed along with the triglycerides.

There are reports disclosing the production of hydrocarbons from oils. For example, U.S. Pat. No. 4,300,009 discloses the use of crystalline aluminosilicate zeolites to convert plant oils (e.g., corn oil) to hydrocarbons (e.g., gasoline), and chemicals (e.g., para-xylene). U.S. Pat. No. 4,992,605 discloses the production of hydrocarbon products in the diesel boiling range by hydroprocessing vegetable oils such as canola or sunflower oil. Finally, US 2004/0230085 A1 discloses a process for treating a hydrocarbon component of biological origin by hydrodeoxygenation followed by isomerization.

SUMMARY OF THE INVENTION

One aspect of the invention is a method of making a diesel fuel from a renewable feedstock. In one embodiment, the method includes providing a pretreated renewable feedstock containing organic acid groups which is pretreated to remove contaminants. The acid groups in the pretreated renewable feedstock are neutralized with ammonia or an amine compound. The neutralized feedstock is hydrotreated to form a mixture of n-paraffins, and the ammonia or amine compounds is removed from the mixture of n-paraffins to form a mixture of n-paraffins with a reduced content of ammonia or amine compounds. The mixture of n-paraffins with the reduced content of ammonia or amine compounds is isomerized to form a mixture of n-paraffins and iso-paraffins.

DETAILED DESCRIPTION OF THE INVENTION

Figure 1:
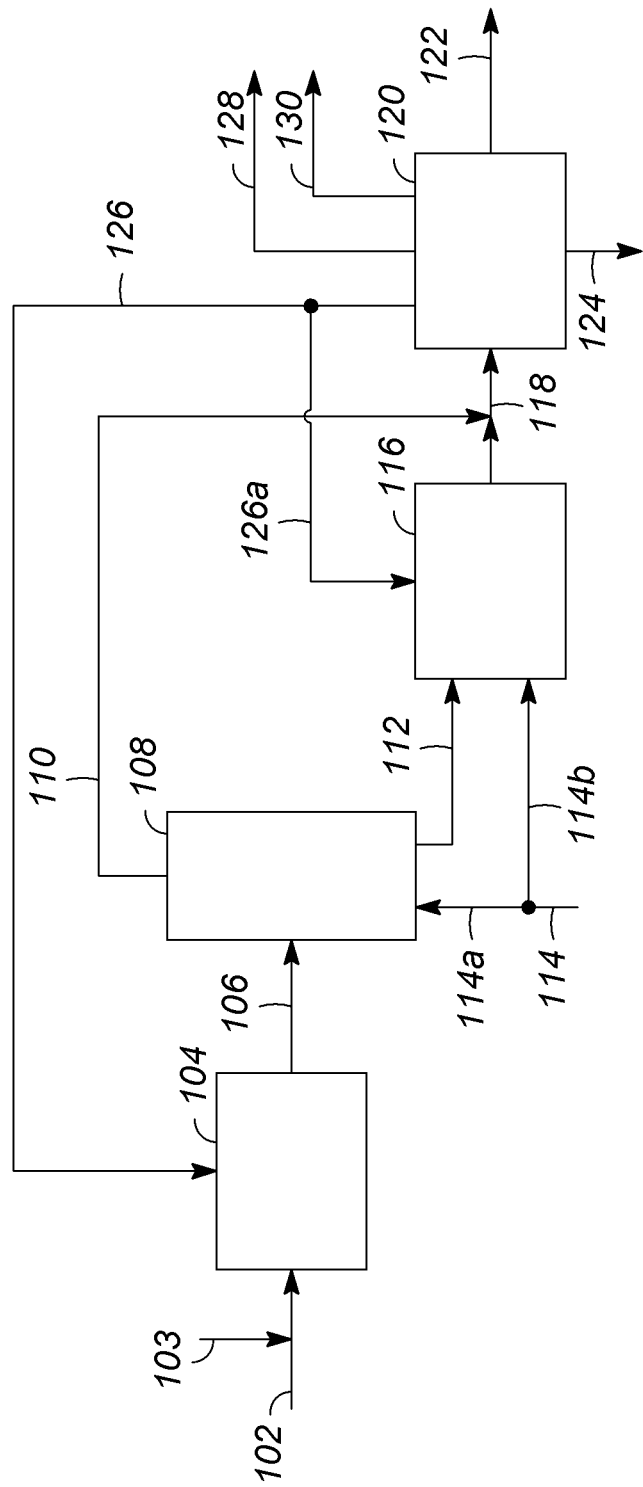
FIG. 1 is a simplified schematic of one embodiment of a process utilizing ammonia or amine compounds.

The present invention relates to a process for producing a hydrocarbon product stream having hydrocarbons with boiling points in the diesel and aviation fuel range from renewable feedstocks originating from plants or animals other than petroleum feedstocks. A process has been developed which includes the use of ammonia or amine compounds to reduce or eliminate potential corrosion and/or fouling problems.

A process has been developed to produce green diesel from natural oils and fats. The process involves deoxygenating renewable feedstocks with carbon chain lengths in the diesel range to produce n-paraffins with both the same number of carbons as the fatty acid chain or one carbon less if the oxygen was removed by decarboxylation. In an optional second stage of the process, the n-paraffins are isomerized to improve the cold properties of the resulting diesel. The basic process is described in U.S. Pat. No. 7,999,142, which is incorporated herein by reference. The optional second stage may also include the isomerization and selective cracking of paraffin to produce a kerosene range jet fuel.

In certain embodiments, such diesel fuel products may be used directly as a fuel, may be blended with other components before being used as diesel fuel, or may receive additives before being used as a diesel fuel. Hydrocarbon products comprising aviation fuel products include hydrocarbons having boiling points in the aviation range, which includes jet range, and may be used directly as aviation fuel or as a blending component to meet the specifications for a specific type of aviation fuel, or may receive additives before being used as an aviation fuel or blending component.

Depending upon the application, various additives may be combined with the aviation component or the diesel component generated in order to meet required specifications for different specific fuels. In particular, the aviation fuel composition generated herein complies with, is a blending component for, or may be combined with one or more additives to meet at least one of various national or international standards such as ASTM D7566 which provides specifications for Aviation Turbine Fuel containing Synthesized Hydrocarbons including up to 50 percent bioderived synthetic blending components—hydroprocessed esters and fatty acids (HEFA)—as additives to conventional jet fuel, ASTM D1655; DEF STAN 91-91; NATO codes F-35, F-34, and/or F-37; JP-8; JP-4; and JP-5, or the general grade requirements for Jet A, Jet A-1, Jet B, and TS-1 fuels as described in the IATA Guidance Material for Aviation Turbine Fuel Specifications. The aviation fuel is generally termed "jet fuel" herein and the term "jet fuel" is meant to encompass aviation fuel that meets the specifications above, and to encompass blending components of an aviation fuel meeting the specifications above. Additives may be added to the jet fuel in order to meet particular specifications. One fuel produced from glycerides or FFA as described herein is very similar to isoparaffinic kerosene or iPK, also known as a synthetic paraffinic kerosene (SPK) or synthetic jet fuel.

It would be desirable to be able to use existing equipment with a variety of feeds without making extensive changes, such as changes in the materials of construction.

However, when a feedstock with high levels of FFAs (or other organic acids) is used, several potential problems can occur. The high acid level could cause corrosion of the feed system, heat exchanger, and/or reactors. In addition, the acid could catalyze undesirable polymerization, fouling, or gumming reactions. Furthermore, hydrotreating reactions of renewable feedstock having significant oxygen content, including triglycerides and FFAs, generate $CO_2$ and water. When the products are cooled down to cold separator temperatures, there is the potential for carbonic acid corrosion.

A co-feed of ammonia or amine compounds can be added in order to reduce or eliminate the impact of corrosion and fouling in the feed system, as well as to mitigate corrosion in the cold separator. The injection of basic anhydrous ammonia, aqueous ammonia, or amine compounds may neutralize the acidity of the FFAs in the feed system, limiting the corrosion potential and fouling potential in the feed system. The ammonia/amine compounds will pass through the hydrotreating zone. The amine compound may react on the first stage catalyst to form ammonia. Because this reaction competes with the deoxygenation reaction, it may be desirable to use ammonia rather than an amine compound. In addition, ammonia may be easier to remove than amine compounds.

The ammonia/amine compounds can be separated from the n-paraffins in a stripper column. The stripper will separate a liquid phase mixture of n-paraffins from a gas stream containing the ammonia/amine compounds.

The ammonia/amine compounds will condense in the product separator zone. The ammonia/amine compounds will provide buffering for the sour water against carbonic acid corrosion in the product separator zone. Although not wishing to be bound by theory, it is believed that the ammonia/amine compounds will form ammonia bisulfide salts with $H_2S$ in the reactor effluent.

The use of ammonia or amine compounds could allow for the metallurgy reductions in the process equipment. Currently, the specifications require corrosion resistant metals high in molybdenum, such as stainless steel 304, 316 and 317 in the feed system and stainless steel 304 at the cold separator. The metal specifications could be reduced with the ammonia co-feed system, allowing the use of existing equipment.

In addition, the ammonia co-feed could allow the use of feedstocks with higher levels of FFAs, which otherwise might cause fouling or plugging problems.

In the present process, the ammonia/amine compounds complex with the acids and act as a salt through the process. They can be easily removed from the water in the product separator zone.

As stated, the present invention relates to a process for producing a hydrocarbon stream useful as diesel or kerosene boiling range fuel from renewable feedstocks such as renewable feedstocks originating from plants or animals. Some of these feedstocks are known as renewable fats and oils. The term renewable feedstock is meant to include feedstocks other than those obtained from petroleum crude oil. The renewable feedstocks that can be used in the present invention include any of those which comprise glycerides and free fatty acids (FFA). Most of the glycerides will be triglycerides, but monoglycerides and diglycerides may be present and processed as well. Examples of these feedstocks include, but are not limited to, canola oil, corn oil, soy oils, rapeseed oil, soybean oil, colza oil, tall oil, sunflower oil, hempseed oil, olive oil, linseed oil, coconut oil, castor oil, peanut oil, palm oil, mustard oil, cottonseed oil, jatropha oil, tallow, yellow and brown greases, lard, train oil, fats in milk, fish oil, algal oil, sewage sludge, and the like. Additional examples of renewable feedstocks include non-edible vegetable oils from the group comprising *Jatropha curcas* (Ratanjoy, Wild Castor, Jangli Erandi), *Madhuca indica* (Mohuwa), *Pongamia pinnata* (Karanji Honge), and *Azadiracta indicia* (Neem). The triglycerides and FFAs of the typical vegetable or animal fat contain aliphatic hydrocarbon chains in their structure which have about 8 to about 24 carbon atoms, with a majority of the fats and oils containing high concentrations of fatty acids with 16 and 18 carbon atoms Mixtures or co-feeds of renewable feedstocks and petroleum derived hydrocarbons may also be used as the feedstock. Other feedstock components which may be used, especially as a co-feed component in combination with the above listed feedstocks, include spent motor oils and industrial lubricants, used paraffin waxes, liquids derived from the gasification of coal, biomass, or natural gas followed by a downstream liquefaction step such as Fischer-Tropsch technology, liquids derived from depolymerization, thermal or chemical, of waste plastics such as polypropylene, high density polyethylene, and low density polyethylene; and other synthetic oils generated as byproducts from petrochemical and chemical processes. Mixtures of the above feedstocks may also be used as co-feed components. In some applications, an advantage of using a co-feed component is the transformation of what may have been considered to be a waste product from a petroleum based or other process into a valuable co-feed component to the current process.

Renewable feedstocks that can be used in the present invention may contain a variety of impurities. The renewable feedstocks may contain contaminants such as alkali metals, e.g. sodium and potassium, phosphorous as well as solids, water and detergents. The feedstock is pretreated to remove contaminants. By "pretreated to remove contaminants," we mean that the amount of contaminants is reduced compared to the initial feedstock. It is desirable to remove as enough of the contaminants to allow for reasonable operation and catalyst life; complete removal is not required.

One possible pretreatment step involves contacting the renewable feedstock with an ion-exchange resin in a pretreatment zone at pretreatment conditions. The ion-exchange resin is an acidic ion exchange resin such as Amberlyst™15 and can be used as a bed in a reactor through which the feedstock is flowed through, either upflow or downflow.

Another possible means for removing contaminants is a mild acid wash. This is carried out by contacting the feedstock with an acid such as sulfuric, nitric or hydrochloric acid in a reactor. The acid and feedstock can be contacted either in a batch or continuous process. Contacting is done with a dilute acid solution usually at ambient temperature and atmospheric pressure. If the contacting is done in a continuous manner, it is usually done in a counter current manner. Yet another possible means of removing metal contaminants from the feedstock is through the use of guard beds which are well known in the art. These can include alumina guard beds either with or without demetallation catalysts such as nickel or cobalt. Filtration and solvent extraction techniques are other choices which may be employed. Hydroprocessing such as that described in U.S. Pat. No. 7,638,040, hereby incorporated by reference, is another pretreatment technique which may be employed.

The ammonia or amine compound can be added to the pretreated feedstock stream before the stream enters feed tank, after it flows out of feed tank, or it can be fed into feed tank. The renewable feedstock is flowed to a first reaction zone comprising one or more catalyst beds in one or more reactors. In the reaction first zone, the pretreated renewable feedstock with the ammonia/amine compound is contacted with a hydrogenation or hydrotreating catalyst in the presence of hydrogen at hydrogenation conditions to hydrogenate the reactive components such as olefinic or unsaturated portions of the n-paraffinic chains. Hydrogenation and hydrotreating catalysts are any of those well known in the art such as nickel or nickel/molybdenum dispersed on a high surface area support. Other hydrogenation catalysts include one or more noble metal catalytic elements dispersed on a high surface area support. Non-limiting examples of noble metals include Pt and/or Pd dispersed on gamma-alumina or activated carbon. Hydrogenation conditions include a temperature of about 40° C. to about 500° C. and a pressure of about 689 kPa absolute (100 psia) to about 13,790 kPa absolute (2000 psia). Other operating conditions for the hydrogenation zone are well known in the art.

The catalysts enumerated above are also capable of catalyzing decarboxylation, decarbonylation and/or hydrodeoxygenation of the feedstock to remove oxygen. Decarboxylation, decarbonylation, and hydrodeoxygenation are herein collectively referred to as deoxygenation reactions. Decarboxylation conditions include a relatively low pressure of about 689 kPa (100 psia) to about 6895 kPa (1000 psia), a temperature of about 200° C. to about 460° C. and a liquid hourly space velocity of about 0.5 to about 10 $hr^{-1}$. Since hydrogenation is an exothermic reaction, as the feedstock flows through the catalyst bed the temperature increases and decarboxylation and hydrodeoxygenation will begin to occur. Thus, it is envisioned and is within the scope of this invention that all the reactions occur simultaneously in one reactor or in one bed. Alternatively, the conditions can be controlled such that hydrogenation primarily occurs in one bed and decarboxylation and/or hydrodeoxygenation occurs in a second bed. Of course if only one bed is used, then hydrogenation occurs primarily at the front of the bed, while decarboxylation/hydrodeoxygenation occurs mainly in the middle and bottom of the bed. Finally, desired hydrogenation can be carried out in one reactor, while decarboxylation, decarbonylation, and/or hydrodeoxygenation can be carried out in a separate reactor.

The effluent from the deoxygenation reactor is conducted to a hot high pressure hydrogen stripper. The reaction product from the deoxygenation reactions will comprise both a liquid portion and a gaseous portion. The liquid portion comprises a hydrocarbon fraction which is essentially all n-paraffins and having a large concentration of paraffins in the range of about 9 to about 18 carbon atoms. The gaseous portion comprises the ammonia/amine compound, hydrogen, carbon dioxide, carbon monoxide, water vapor, propane, and perhaps sulfur components, such as hydrogen sulfide, or phosphorous components, such as phosphine. One purpose of the hot high pressure hydrogen stripper is to selectively separate at least a portion of the gaseous portion of the effluent containing the ammonia/amine compound from the liquid portion of the effluent.

Failure to remove the ammonia/amine compounds, water, carbon monoxide, and carbon dioxide from the effluent may result in poor catalyst performance in the isomerization zone. Water, carbon monoxide, carbon dioxide, the ammonia/amine compounds, or hydrogen sulfide are selectively stripped in the hot high pressure hydrogen stripper using hydrogen. The hydrogen used for the stripping may be dry, and free of carbon oxides.

The temperature may be controlled in a limited range to achieve the desired separation and the pressure may be maintained at approximately the same pressure as the two reaction zones to minimize both investment and operating costs. The hot high pressure hydrogen stripper may be operated at conditions ranging from a pressure of about 689 kPa absolute (100 psia) to about 13,790 kPa absolute (2000 psia), and a temperature of about 40° C. to about 350° C. The hot high pressure hydrogen stripper may be operated at essentially same pressure as the reaction zone. By "essentially", it is meant that the operating pressure of the hot high pressure hydrogen stripper is within about 1034 kPa absolute (150 psia) of the operating pressure of the reaction zone. For example, in one embodiment the hot high pressure hydrogen stripper separation zone is no more than 1034 kPa absolute (150 psia) less than that of the reaction zone.

The effluent from the deoxygenation reaction enters the hot high pressure stripper, and at least a portion of the gaseous components are carried with the hydrogen stripping gas and separated into an overhead stream. The remainder of the deoxygenation zone effluent stream is removed as hot high pressure hydrogen stripper bottoms and contains the liquid hydrocarbon fraction having components such as normal hydrocarbons having from about 8 to about 24 carbon atoms. Different feedstocks will result in different distributions of paraffins. A portion of this liquid hydrocarbon fraction in hot high pressure hydrogen stripper bottoms may be used as the hydrocarbon recycle described below.

Hydrogen may be separated from process effluent(s) and recycled to the hydrogenation and deoxygenation zone, or the amount of hydrogen may be in only slight excess, about 5 to about 25%, of the hydrogen requirements of the hydrogenation and deoxygenation reactions and therefore not recycled. Another refinery unit, such as a hydrocracker, may be used as a source of hydrogen, which potentially eliminates the need for a recycle gas compressor.

In one embodiment, the desired amount of hydrogen is kept in solution at lower pressures by employing a large recycle of hydrocarbon to the deoxygenation reaction zone. Other processes have employed hydrocarbon recycle in order to control the temperature in the reaction zones since the reactions are exothermic reactions. However, the range of recycle to feedstock ratios is determined not on temperature control requirements, but instead, based upon hydrogen solubility requirements. Hydrogen has a greater solubility in the hydrocarbon product than it does in the feedstock. By utilizing a large hydrocarbon recycle, the solubility of hydrogen in the combined liquid phase in the reaction zone is greatly increased, and higher pressures are not needed to increase the amount of hydrogen in solution. In one embodiment of the invention, the volume ratio of hydrocarbon recycle to feedstock is from about 2:1 to about 8:1, or 2:1 to about 6:1. In another embodiment, the ratio is in the range of about 3:1 to about 6:1, and in yet another embodiment, the ratio is in the range of about 4:1 to about 5:1.

Although the hydrocarbon fraction separated in the hot high pressure hydrogen stripper is useful as a diesel boiling range fuel, it will have poor cold flow properties because it comprises essentially n-paraffins. The hydrocarbon fraction can be contacted with an isomerization catalyst under isomerization conditions to at least partially isomerize the n-paraffins to branched paraffins to improve the cold flow properties. The effluent of the second reaction zone, the isomerization zone, is a branched-paraffin-rich stream. By the term "rich" it is meant that the effluent stream has a greater concentration of branched paraffins than the stream entering the isomerization zone, and preferably comprises greater than 50 mass-% branched paraffins. It is envisioned that the isomerization zone effluent may contains 70, 80, or 90 mass-% branched paraffins.

Isomerization can be carried out in a separate bed of the same reaction zone, i.e., same reactor described above for deoxygenation, or the isomerization can be carried out in a separate reactor. For ease of description, an embodiment with a second reactor for the isomerization reaction will be described. The hydrogen stripped product of the deoxygenation reaction zone is contacted with an isomerization catalyst in the presence of hydrogen at isomerization conditions to isomerize the normal paraffins to branched paraffins. Only minimal branching is required, sufficient to overcome the cold-flow problems of the normal paraffins. Because attempting to obtain significant branching runs the risk of undesired cracking, the predominant isomerized product is a monobranched hydrocarbon. Alternatively, the isomerization and selective cracking of paraffin to produce a kerosene range jet fuel may be employed. The isomerization of the paraffinic product can be accomplished in any manner known in the art or by using any suitable catalyst known in the art. One or more beds of catalyst may be used. It is preferred that the isomerization be operated in a co-current mode of operation. Fixed bed, trickle bed down flow or fixed bed liquid filled up-flow modes are both suitable. See also, for example, US 2004/0230085 A1 which is incorporated by reference in its entirety. Suitable catalysts comprise a metal of Group VIII (IUPAC8-10) of the Periodic Table and a support material. Suitable Group VIII metals include platinum and palladium, each of which may be used alone or in combination. The support material may be amorphous or crystalline. Suitable support materials include, but are not limited to, amorphous alumina, amorphous silica-alumina, ferrierite, ALPO-31, SAPO-11, SAPO-31, SAPO-37, SAPO-41, SM-3, MgAPSO-31, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MgAPSO-11, MgAPSO-31, MgAPSO-41, MgAPSO-46, ELAPO-11, ELAPO-31, ELAPO-41, ELAPSO-11, ELAPSO-31, ELAPSO-41, laumontite, cancrinite, offretite, hydrogen form of stillbite, magnesium or calcium form of mordenite, and magnesium or calcium form of partheite, each of which may be used alone or in combination. ALPO-31 is described in U.S. Pat. No. 4,310,440. SAPO-11, SAPO-31, SAPO-37, and SAPO-41 are described in U.S. Pat. No. 4,440,871. SM-3 is described in U.S. Pat. Nos. 4,943,424; 5,087,347; 5,158,665; and 5,208,005. MgAPSO is a MeAPSO, which is an acronym for a metal aluminumsilicophosphate molecular sieve, where the metal Me is magnesium (Mg). Suitable MgAPSO-31 catalysts include MgAPSO-31. MeAPSOs are described in U.S. Pat. No. 4,793,984, and MgAPSOs are described in U.S. Pat. No. 4,758,419. MgAPSO-31 is a preferred MgAPSO, where 31 means a MgAPSO having structure type 31. Many natural zeolites, such as ferrierite, that have an initially reduced pore size can be converted to forms suitable for olefin skeletal isomerization by removing associated alkali metal or alkaline earth metal by ammonium ion exchange and calcination to produce the substantially hydrogen form, as taught in U.S. Pat. No. 4,795,623 and U.S. Pat. No. 4,924,027. Further catalysts and conditions for skeletal isomerization are disclosed in U.S. Pat. Nos. 5,510,306; 5,082,956; and 5,741,759.

The isomerization catalyst may also comprise a modifier selected from lanthanum, cerium, praseodymium, neodymium, samarium, gadolinium, terbium, and mixtures thereof, as described in U.S. Pat. Nos. 5,716,897 and 5,851,949. Other suitable support materials include ZSM-22, ZSM-23, and ZSM-35, which are described for use in dewaxing in U.S. Pat. No. 5,246,566 and in the article entitled "New molecular sieve process for lube dewaxing by wax isomerization," written by S. J. Miller, in Microporous Materials 2 (1994) 439-449. The teachings of U.S. Pat. Nos. 4,310,440; 4,440,871; 4,793,984; 4,758,419; 4,943,424; 5,087,347; 5,158,665; 5,208,005; 5,246,566; 5,716,897; and 5,851,949 are hereby incorporated by reference.

U.S. Pat. Nos. 5,444,032 and 5,608,968 teach a suitable bifunctional catalyst which is constituted by an amorphous silica-alumina gel and one or more metals belonging to Group VIIIA, and which is effective in the hydroisomerization of long-chain normal paraffins containing more than 15 carbon atoms. An activated carbon catalyst support may also be used. U.S. Pat. Nos. 5,981,419 and 5,908,134 teach a suitable bifunctional catalyst which comprises: (a) a porous crystalline material isostructural with beta-zeolite selected from boro-silicate (BOR-B) and boro-alumino-silicate (Al-BOR-B) in which the molar $SiO_2:Al_2O_3$ ratio is higher than 300:1; (b) one or more metal(s) belonging to Group VIIIA, selected from platinum and palladium, in an amount comprised within the range of from 0.05 to 5% by weight. Article V. Calemma et al., App. Catal. A: Gen., 190 (2000), 207 teaches yet another suitable catalyst.

The isomerization catalyst may be any of those well known in the art such as those described and cited above. Isomerization conditions include a temperature of about 150° C. to about 450° C. and a pressure of about 1724 kPa absolute (250 psia) to about 4726 kPa absolute (700 psia). Other operating conditions for the isomerization zone are well known in the art. Operating at low pressures allows for the optional introduction of hydrogen from another unit, such as a hydrogen plant, without the use of a make-up compressor which may be an option to reduce or eliminate hydrogen recycle. When hydrogen is not recycled, the amount of hydrogen introduced to the isomerization zone would be only slightly greater than that which is consumed, for example, an excess of about 5 to about 25 percent of the consumption requirements.

The final effluent stream, i.e. the stream obtained after all reactions have been carried out, is now processed through one or more separation steps to obtain a purified hydrocarbon stream useful as a diesel or jet fuel. With the final effluent stream comprising both a liquid component and a gaseous component, various portions of which are to be recycled, multiple separation steps may be employed. For example, hydrogen may be first separated in an isomerization effluent separator with the separated hydrogen being removed in an overhead stream. Suitable operating conditions of the isomerization effluent separator include, for example, a temperature of 230° C. and a pressure of 4100 kPa absolute (600 psia). If there is a low concentration of carbon oxides, or the carbon oxides are removed, the hydrogen may be recycled back to the hot high pressure hydrogen stripper for use both as a stripping gas and to combine with the remainder as a bottoms stream. The remainder is passed to the isomerization reaction zone, and the hydrogen becomes a component of the isomerization reaction zone feed streams in order to provide the necessary hydrogen partial pressures for the reactor. The hydrogen is also a reactant in the deoxygenation reactors, and different feedstocks will consume different amounts of hydrogen. The isomerization effluent separator allows flexibility for the process to operate even when larger amounts of hydrogen are consumed in the first reaction zone. Furthermore, at least a portion of the remainder or bottoms stream of the isomerization effluent separator may be recycled to the isomerization reaction zone to increase the degree of isomerization.

The remainder of the final effluent after the removal of hydrogen still has liquid and gaseous components and is cooled by techniques such as air cooling or water cooling, and passed to a cold separator where the liquid component is separated from the gaseous component. Suitable operating conditions of the cold separator include, for example, a temperature of about 20 to 60° C. and a pressure of 3850 kPa absolute (560 psia). A water byproduct stream is also separated. At least a portion of the liquid component, after cooling and separating from the gaseous component, may be recycled back to the isomerization zone to increase the degree of isomerization. Prior to entering the cold separator, the remainder of the final effluent stream may be combined with the hot high pressure hydrogen stripper overhead stream, and the resulting combined stream may be introduced into the cold separator.

The liquid component contains the hydrocarbons useful as diesel or jet fuel, termed diesel fuel range hydrocarbons and aviation fuel range hydrocarbons respectively, as well as smaller amounts of naphtha and liquefied petroleum gas (LPG). The liquid component of the effluent stream is purified in the product fractionation, such as a fractionation zone which separates lower boiling components and dissolved gases into an LPG and naphtha stream; an aviation range product; and a diesel range product. The conditions of the distillation zone include a temperature of from about 20 to about 300° C. at the overhead, and a pressure from about 0 to about 1379 kPa absolute (0 to 200 psia). The conditions of the distillation zone may be adjusted to control the relative amounts of hydrocarbon contained in the aviation range product stream and the diesel range product stream.

The LPG and naphtha stream may be further separated in a debutanizer or depropanizer in order to separate the LPG into an overhead stream, leaving the naphtha in a bottoms stream. Suitable operating conditions of this unit include a temperature of from about 20 to about 200° C. at the overhead, and a pressure from about 0 to about 2758 kPa absolute (0 to 400 psia). The LPG may be sold as valuable product, or it may be used in other processes such as a feed to a hydrogen production facility. Similarly, the naphtha may be used in other processes, such as the feed to a hydrogen production facility, a co-feed to a reforming process, or it may be used as a fuel blending component in the gasoline blending pool, for example.

In another embodiment, the product fractionation may comprise a single fraction column that operates to provide four streams, with the hydrocarbons suitable for use in a diesel fuel removed from the bottom of the column, hydrocarbons suitable for use in an aviation fuel removed from a first side-cut, hydrocarbons in the naphtha range being removed in a second site-cut and the propane and light ends, such as hydrocarbons having carbon chains or 3 or fewer carbons, being removed in an overhead from the column.

In yet another embodiment, the product fractionation may include multiple fractionation columns, with a first fractionation column separating the hydrocarbons useful in diesel and aviation fuels into a bottoms stream, and propane, light ends, and naphtha into an overhead stream. A second fractionation column may be used to separate the hydrocarbons suitable for use in a diesel fuel into a bottoms stream of the column and hydrocarbons suitable for use in an aviation fuel into an overhead stream of the column, while a third fractionation column may be employed to separate the naphtha range hydrocarbons from the propane and light ends. Also, dividing wall columns may be employed. The operating conditions of the one or more fractionation columns may be used to control the amount of the hydrocarbons that are withdrawn in each of the streams as well as the composition of the hydrocarbon mixture withdrawn in each stream. Typical operating variables well known in the distillation art include column temperature, column pressure, reflux ratio, and the like. The result of changing column variables, however, is only to adjust the vapor temperature at the top of the distillation column. Therefore, the distillation variables are adjusted with respect to a particular feedstock in order to achieve a temperature cut point to give a product that meets desired properties.

The gaseous component separated in the product separator comprises mostly hydrogen, the carbon dioxide from the decarboxylation reaction, and the ammonia/amine compound. Other components such as carbon monoxide, propane, and hydrogen sulfide or other sulfur containing component may be present as well.

It is desirable to recycle the hydrogen to the reaction zone, but if the carbon dioxide was not removed, its concentration would quickly build up and effect the operation of the reaction zone. The carbon dioxide can be removed from the hydrogen by means well known in the art such as reaction with amine solutions, a hot carbonate solution, pressure swing absorption, etc. If desired, essentially pure carbon dioxide can be recovered by regenerating the spent absorption media.

The ammonia/amine compounds can be removed using amine absorbers. The ammonia/amine compounds can be recycled for reuse in the process.

Similarly, a sulfur containing component such as hydrogen sulfide may be present to maintain the sulfided state of the deoxygenation catalyst or to control the relative amounts of the decarboxylation reaction and the hydrogenation reaction that are both occurring in the deoxygenation zone. The amount of sulfur is generally controlled, and it can be removed before the hydrogen is recycled. The sulfur components may be removed using techniques such as absorption with an amine or by caustic wash. Of course, depending upon the technique used, the carbon dioxide and sulfur containing components, and other components, may be removed in a single separation step such as a hydrogen selective membrane.

The hydrogen remaining after the removal of at least carbon dioxide may be recycled to the reaction zone where hydrogenation primarily occurs and/or to any subsequent beds or reactors. The recycle stream may be introduced to the inlet of the reaction zone and/or to any subsequent beds or reactors. One benefit of the hydrocarbon recycle is to control the temperature rise across the individual beds. However, as discussed above, the amount of hydrocarbon recycle may be determined based upon the desired hydrogen solubility in the reaction zone which is in excess of that used for temperature control. Increasing the hydrogen solubility in the reaction mixture allows for successful operation at lower pressures, and thus reduced cost.

The following embodiment is presented in illustration and is not intended as an undue limitation on the generally broad scope of the invention as set forth in the claims. The process is first described in general with reference to FIG. 1. It is then described in more detail with reference to FIG. 2.

Turning to FIG. 1, pretreated renewable feedstock 102 is combined with ammonia/amine compound stream 103. The combined stream enters deoxygenation reaction zone 104 along with recycle hydrogen 126. Deoxygenated product 106 is stripped in hot high pressure hydrogen stripper 108 using hydrogen 114a. The ammonia/amine compounds, carbon oxides, and water vapor are removed with hydrogen in overhead 110. Selectively stripped deoxygenated product 112 is passed to isomerization zone 116 along with recycle hydrogen 126a and make-up hydrogen 114b. Isomerized product 118 is combined with overhead 110 and passed to product recovery zone 120. The presence of the ammonia/amine compounds in the product recovery zone 120 provides buffering for the sour water against carbonic acid corrosion.

Carbon oxide stream 128, light ends stream 130, ammonia/amine compound-water byproduct stream 124, hydrogen stream 126, and branched paraffin-rich product 122 are removed from product recover zone 120. Branched paraffin-rich product 122 may be collected for use as diesel fuel, and hydrogen stream 126 is recycled to the deoxygenation reaction zone 104. The ammonia/amine compounds can be separated from the water and recycled.

Figure 2:
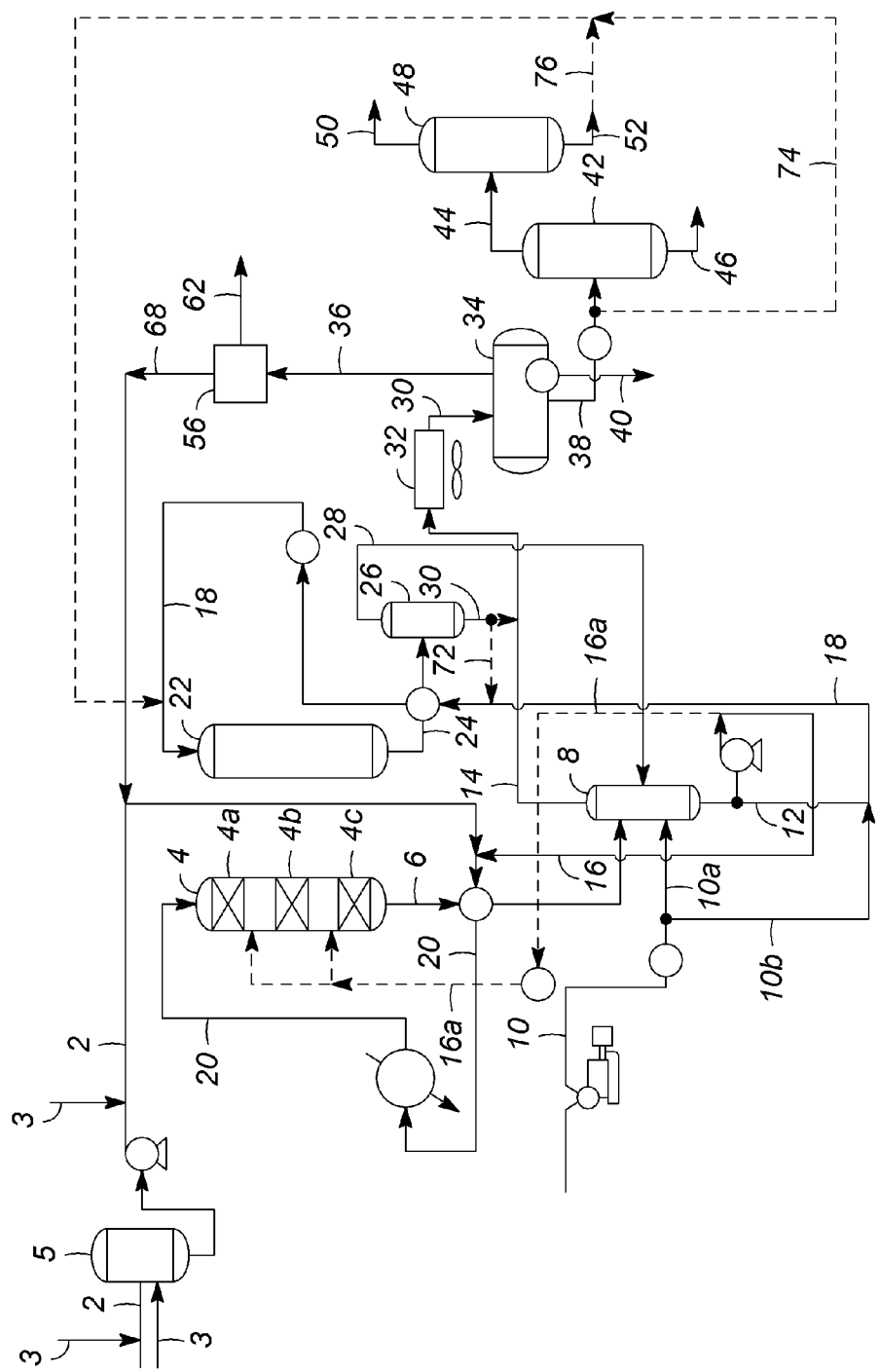
FIG. 2 is a detailed schematic of one embodiment of a process using ammonia or amine compounds.

Turning to FIG. 2, the process begins with a pretreated renewable feedstock stream 2 which may pass through an optional feed surge drum 5. The ammonia/amine compounds stream 3 is added to the pretreated feedstock stream 2 before the feed surge drum 5, after the feed surge drum 5, or into the feed surge drum 5.

The feedstock stream 2 is combined with recycle gas stream 68 and recycle stream 16 to form combined feed stream 20, which is heat exchanged with reactor effluent and then introduced into deoxygenation reactor 4. The heat exchange may occur before or after the recycle is combined with the feed. Deoxygenation reactor 4 may contain multiple beds shown in FIG. 2 as 4a, 4b and 4c. Deoxygenation reactor 4 contains at least one catalyst capable of catalyzing decarboxylation and/or hydrodeoxygenation of the feedstock to remove oxygen. Deoxygenation reactor effluent stream 6 containing the products of the decarboxylation and/or hydrodeoxygenation reactions as well as the ammonia/amine compounds is removed from deoxygenation reactor 4 and heat exchanged with stream 20 containing feed to the deoxygenation reactor 4. Stream 6 comprises a liquid component containing largely normal paraffin hydrocarbons in the diesel boiling range and a gaseous component containing largely hydrogen, ammonia/amine compounds, vaporous water, carbon monoxide, carbon dioxide and propane.

Deoxygenation reactor effluent stream 6 is then directed to hot high pressure hydrogen stripper 8. Make up hydrogen in line 10 is divided into two portions, streams 10a and 10b. Make up hydrogen in stream 10a is also introduced to hot high pressure hydrogen stripper 8. In hot high pressure hydrogen stripper 8, the gaseous component of deoxygenation reactor effluent 6 is selectively stripped from the liquid component of deoxygenation reactor effluent 6 using make-up hydrogen 10a and recycle hydrogen 28. The dissolved gaseous component comprising hydrogen, ammonia/amine compound, vaporous water, carbon monoxide, carbon dioxide and at least a portion of the propane, is selectively separated into hot high pressure hydrogen stripper overhead stream 14. The remaining liquid component of deoxygenation reactor effluent 6 comprising primarily normal paraffins having a carbon number from about 8 to about 24 with a cetane number of about 60 to about 100 is removed as hot high pressure hydrogen stripper bottom 12.

A portion of hot high pressure hydrogen stripper bottoms forms recycle stream 16 and is combined with renewable feedstock stream 2 to create combined feed 20. Another portion of recycle stream 16, optional stream 16a, may be routed directly to deoxygenation reactor 4 and introduced at interstage locations such as between beds 4a and 4b and/or between beds 4b and 4c to aid in temperature control, for example. The remainder of hot high pressure hydrogen stripper bottoms in stream 12 is combined with hydrogen stream 10b to form combined stream 18 which is routed to isomerization reactor 22. Stream 18 may be heat exchanged with isomerization reactor effluent 24.

The product of the isomerization reactor containing a gaseous portion of hydrogen and propane and a branched-paraffin-rich liquid portion is removed in line 24, and after optional heat exchange with stream 18, is introduced into hydrogen separator 26. The overhead stream 28 from hydrogen separator 26 contains primarily hydrogen which may be recycled back to hot high pressure hydrogen stripper 8. Bottom stream 30 from hydrogen separator 26 is air cooled using air cooler 32 and introduced into product separator 34. In product separator 34, the gaseous portion of the stream comprising hydrogen, ammonia/amine compounds, carbon monoxide, hydrogen sulfide, carbon dioxide and propane are removed in stream 36 while the liquid hydrocarbon portion of the stream is removed in stream 38. A water byproduct stream 40 containing most of the ammonia/amine compounds may also be removed from product separator 34. Stream 38 is introduced to product stripper 42 where components having higher relative volatilities are separated into stream 44 with the remainder, the diesel range components, being withdrawn from product stripper 42 in line 46. Stream 44 is introduced into fractionator 48 which operates to separate LPG into overhead 50 leaving a naphtha bottoms 52. Any of optional lines 72, 74, or 76 may be used to recycle at least a portion of the isomerization zone effluent back to the isomerization zone to increase the amount of n-paraffins that are isomerized to branched paraffins.

The vapor stream 36 from product separator 34 contains the gaseous portion of the isomerization effluent which comprises at least hydrogen, carbon monoxide, hydrogen sulfide, carbon dioxide and propane (possibly with small amounts of ammonia/amine compounds) and is directed to a system of amine absorbers to separate carbon dioxide and hydrogen sulfide from the vapor stream. Because of the cost of hydrogen, it is desirable to recycle the hydrogen to deoxygenation reactor 4, but it is not desirable to circulate the carbon dioxide or an excess of sulfur containing components. In order to separate carbon dioxide from the hydrogen, vapor stream 36 is passed through an amine absorber, also called a scrubber, in zone 56. The amine chosen to be employed in the amine scrubber 56 is capable of selectively removing at least carbon dioxide. Suitable amines are available from DOW and from BASF, and in one embodiment the amines are a promoted or activated methyldiethanolamine (MDEA). See U.S. Pat. No. 6,337,059, which is hereby incorporated by reference in its entirety. Suitable amines DOW include the UCARSOL™ AP series solvents such as AP802, AP804, AP806, AP810 and AP814. The carbon dioxide is absorbed by the amine while the hydrogen passes through the amine scrubber zone and into line 68 to be recycled to the first reaction zone. The amine is regenerated, and the carbon dioxide is released and removed in line 62. Within the amine absorber zone, regenerated amine may be recycled for use again. Conditions for the scrubber zone include a temperature in the range of 30 to 60° C. The absorber is operated at essentially the same pressure as the reaction zone. By "essentially" it is meant that the operating pressure of the first absorber is within about 1034 kPa absolute (150 psia) of the operating pressure of the reaction zone. For example, the pressure of the absorber is no more than 1034 kPa absolute (150 psia) less than that of the reaction zone.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of making a diesel fuel from a renewable feedstock comprising:

providing a pretreated renewable feedstock containing organic acid groups, the pretreated renewable feedstock pretreated to remove contaminants;

neutralizing the acid groups in the pretreated renewable feedstock with ammonia or an amine compound;

hydrotreating the neutralized feedstock to form a mixture of n-paraffins;

removing the ammonia or amine compounds from the mixture of n-paraffins to form a mixture of n-paraffins with a reduced content of ammonia or amine compounds; and isomerizing the mixture of n-paraffins with a reduced content of ammonia or amine compounds to form a mixture of n-paraffins and iso-paraffins.

2. The method of claim 1 wherein neutralizing the acid groups comprises introducing the ammonia or amine compound into a feedstream containing the pretreated renewable feedstock.

3. The method of claim 2 wherein the ammonia or amine compound is introduced into the feedstream before the feedstream enters a storage tank.

4. The method of claim 2 wherein the ammonia or amine compound is introduced into the feedstream after the feedstream enters a storage tank.

5. The method of claim 1 wherein neutralizing the acid groups comprises introducing the ammonia or amine compound into a storage tank containing the pretreated renewable feedstock.

6. The method of claim 5 wherein the storage tank has a nitrogen blanket.

7. The method of claim 1 wherein the acid groups are neutralized with the ammonia.

8. The method of claim 1 wherein the renewable feedstock comprises glycerides and free fatty acids.

9. The method of claim 1 wherein the renewable feedstock comprises liquid from gasification of biomass.

10. The method of claim 1 wherein removing the ammonia or amine compounds comprises stripping the mixture of n-paraffins in a stripping column to form a gas stream containing the ammonia or amine compounds and a liquid phase mixture of n-paraffins with reduced content of ammonia or amine compounds.

11. The method of claim 10, further comprising cooling the gas stream to condense water, the water containing the ammonia or amine compounds.

12. The method of claim 11, wherein the ammonia or amine compounds neutralize acidity in the water.

13. A method of making a diesel fuel from a renewable feedstock comprising:

providing a pretreated renewable feedstock containing organic acid groups, the pretreated renewable feedstock pretreated to remove contaminants;

introducing ammonia or an amine compound into a feedstream containing the pretreated renewable feedstock to neutralize the acid groups in the pretreated renewable feedstock;

hydrotreating the neutralized feedstock to form a mixture of n-paraffins;

stripping the mixture of n-paraffins in a stripping column to form a gas stream containing the ammonia or amine compounds and a liquid phase mixture of n-paraffins with reduced content of ammonia or amine compounds; and isomerizing the mixture of n-paraffins with a reduced content of ammonia or amine compounds to form a mixture of n-paraffins and iso-paraffins.

14. The method of claim 13, further comprising cooling the gas stream to condense water, the water containing the ammonia or amine compounds.

15. The method of claim 14, wherein the ammonia or amine compounds neutralize acidity in the water.

16. The method of claim 13 wherein the acid groups are neutralized with the ammonia.

17. The method of claim 13 wherein the renewable feedstock comprises glycerides and free fatty acids.

18. The method of claim 13 wherein the renewable feedstock comprises liquid from gasification of biomass.

19. The method of claim 13 wherein the ammonia or amine compound is introduced into the feedstream before the feedstream enters a storage tank.

20. The method of claim 13 wherein neutralizing the acid groups comprises introducing the ammonia or amine compound into a storage tank containing the pretreated renewable feedstock.

* * * * *